US00RE33906E

United States Patent [19]

Vecchietti et al.

[11] E Patent Number: Re. 33,906

[45] Reissued Date of Patent: Apr. 28, 1992

[54] CYCLIC CARBOXAMIDE DERIVATIVES AND THEIR USE AS ANALGESICS

[75] Inventors: Vittorio Vecchietti; Massimo Signorini, both of Milan; Antonio Giordani, Pavia, all of Italy

[73] Assignee: Dr.Lo.Zambeletti S.p.A., Italy

[21] Appl. No.: 562,887

[22] Filed: Aug. 3, 1990

Related U.S. Patent Documents

Reissue of:

[64] Patent No.: 4,801,585
Issued: Jan. 31, 1989
Appl. No.: 945,038
Filed: Dec. 22, 1986

[30] Foreign Application Priority Data

Dec. 23, 1985 [GB] United Kingdom ..... 8531617
Sep. 2, 1986 [GB] United Kingdom ..... 8621136

[51] Int. Cl.[5] ..... A61K 31/55; A61K 31/445; C07D 401/06

[52] U.S. Cl. ..... 514/212; 514/210; 514/316; 514/326; 514/422; 514/408; 540/450; 540/480; 540/596; 540/607; 546/189; 546/208; 546/245; 548/518; 548/540

[58] Field of Search ..... 514/210, 212, 316, 317, 514/326; 546/189, 208, 243; 540/450, 480, 596, 607; 548/518, 540

[56] References Cited

U.S. PATENT DOCUMENTS

| | | | |
|---|---|---|---|
| 2,684,965 | 7/1954 | Weston et al. | 546/189 |
| 3,468,892 | 9/1969 | Tomcufcik et al. | 546/208 |
| 4,339,576 | 7/1982 | Zenitz | 548/224 |
| 4,499,286 | 2/1985 | Binder | 548/527 |
| 4,588,585 | 1/1989 | Ingendoh et al. | 514/322 |
| 4,753,952 | 6/1988 | Vecchietti et al. | 514/307 |
| 4,806,547 | 2/1989 | Giardina et al. | 514/307 |
| 4,826,819 | 5/1989 | Vecchietti et al. | 514/331 |
| 4,879,300 | 11/1989 | Giordani et al. | 546/189 |
| 4,994,450 | 2/1991 | Vecchietti et al. | 540/596 |

FOREIGN PATENT DOCUMENTS

| | | |
|---|---|---|
| 52311 | 5/1980 | European Pat. Off. . |
| 0146297 | 6/1985 | European Pat. Off. . |
| 232612 | 8/1987 | European Pat. Off. . |
| 1645897 | 9/1970 | Fed. Rep. of Germany . |
| 1250719 | 10/1971 | United Kingdom . |
| 1500225 | 2/1978 | United Kingdom . |
| 1569225 | 6/1980 | United Kingdom . |

*Primary Examiner*—Donald G. Daus
*Attorney, Agent, or Firm*—Rosenman & Colin

[57] ABSTRACT

A compound of formula (I):

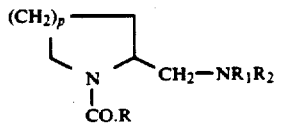

(I)

or a salt or solvate thereof in which R. CO is an acyl group containing a substituted or unsubstituted carbocyclic or heterocyclic aromatic ring, $R_1$ and $R_2$ are independently $C_{1-6}$ alkyl or together form a $C_{3-6}$ polymethylene or alkylene group, and p is 1, 2, 3 or 4, is useful for treating pain.

10 Claims, No Drawings

CYCLIC CARBOXAMIDE DERIVATIVES AND THEIR USE AS ANALGESICS

Matter enclosed in heavy brackets [ ] appears in the original patent but forms no part of this reissue specification; matter printed in italics indicates the additions made by reissue.

This invention is concerned with novel azacyclic derivatives, processes for their preparation, and their use in medicine, particularly as analgesics.

Compounds which are K-receptor agonists act as analgesics through interaction with Kappa opioid receptors. The advantage of K-receptor agonists over the classical $\mu$-receptor agonists, such as morphine, lies in their ability of causing analgesia while being devoid of morphine-like behavioural effects and addiction liability.

We have now discovered a novel class of compounds which exhibit K-receptor agonism without the behavioural effects of morphine and morphine analogues, and which are thus of potential therapeutic utility as analgesics.

According to the present invention there is provided a compound, or a solvate or salt thereof, of formula I:

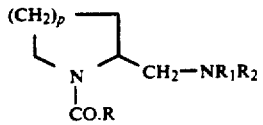

in which: R.CO— is an acyl group containing a substituted or unsubstituted carbocyclic or heterocyclic aromatic ring, $R_1$ and $R_2$ are independently $C_{1-6}$ alkyl groups or together form a $C_{3-6}$ polymethylene or alkenylene group, and p is 1,2,3 or 4.

When $R_1$ and $R_2$ are $C_{1-6}$ alkyl groups, examples are methyl, ethyl, propyl, butyl, pentyl or hexyl groups, preferably methyl.

When $R_1$ and $R_2$ are polymethylene groups, examples are propylene, butylene, pentylene or hexylene, preferably butylene. As an alkenylene group, $R_1$-$R_2$ may be typically $—CH_2—CH{=}CH—CH_2—$.

The group R preferably has the formula (II)

$$—(CHR_4)_n—X—Ar—(R_3)_m \qquad (II)$$

in which n is 0, 1 or 2, m is 1, 1 or 2,

X is a direct bond, or O, S or $NR_5$ in which $R_5$ is hydrogen or $C_{1-6}$ alkyl, Ar is a substituted or unsubstituted carbocyclic or heterocyclic ring, $R_3$ is halogen, such as chloro or fluoro, $C_{1-6}$ alkoxy, cyano, $—COOR_4$, $C_{1-6}$ alkyl, aryl or amino or, when m is 2, two $R_3$'s form a $C_{3-6}$ polymethylene group, and $R_4$ is hydrogen or $C_{1-6}$ alkyl.

Examples of $R_4$ are methyl and ethyl, and preferably $R_4$ is hydrogen.

Preferably Ar is phenyl or 2- or 3-thienyl.

Suitable $R_3$ substitutes for Ar are one or more chlorine atoms, or methyl or methoxy groups. When two $R_3$'s are linked they may form a fused cyclopentyl or cyclohexyl ring.

X is typically oxygen or a direct bond, and n is typically 0 or 1.

Examples of R are:

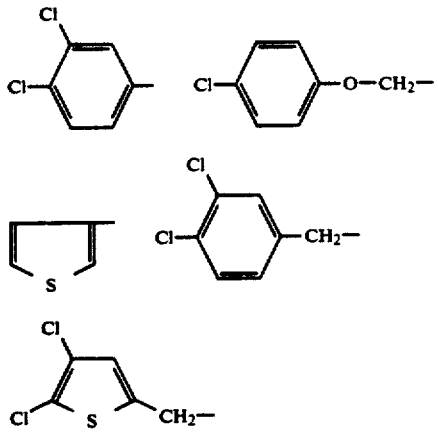

A particularly preferred group of compounds of formula (I) are those in which p=2, i.e. those based on a piperidine ring.

The compounds of formula I or their salts or solvates are preferably in pharmaceutically acceptable or substantially pure form. By pharmaceutically acceptable form is meant, inter alia, of a pharmaceutically acceptable level of purity excluding normal pharmaceutical additives such as diluents and carriers, and including no material considered toxic at normal dosage levels.

A substantially pure form will generally contain at least 50% (excluding normal pharmaceutical additives), preferably 75%, more preferably 90% and still more preferably 95% of the compound of formula I or its salt or solvate.

One preferred pharmaceutically acceptable form is the crystalline form, including such form in a pharmaceutical composition. In the case of salts and solvates the additional ionic and solvent moieties must also be non-toxic.

Examples of a pharmaceutically acceptable salt of a compound of formula I include the acid addition salts with the conventional pharmaceutical acids, for example, maleic, hydrochloric, hydrobromic, phosphoric, acetic, fumaric, salicylic, citric, lactic, mandelic, tartaric, succinic, benzoic, ascorbic and methanesulphonic.

Examples of a pharmaceutically acceptable solvate of a compound of formula I include the hydrate.

The compounds of formula I have at least one asymmetric centre and therefore exist in more than one stereoisomeric form. The invention extends to all such forms and to mixtures thereof, including racemates. The preferred stereoisomeric form is the (S) enantiomer.

The present invention also provide a process for the preparation of a compound of formula I which comprises reacting a compound of formula (III)

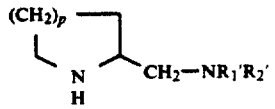

(III)

in which $R_1'$ and $R_2'$ and $R_1$ and $R_2$ as defined for formula (I) or a group or atom convertible to $R_1$ and $R_2$, with a compound of formula

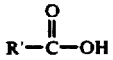

or an active derivative thereof, in which R' is R as defined for formula (I) or a group convertible to R, to form a compound of formula (Ia)

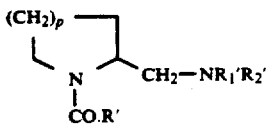

(Ia)

and then performing one or more of the following steps:

(a) where R', $R_1'$ or $R_2'$ are other than R, $R_1$ and $R_2$, converting R', $R_1'$ or $R_2$- to R, $R_1$ or $R_2$ to obtain a compound of formula (I), (b) where R', $R_1'$ and $R_2'$ are R, $R_1$ and $R_2$, converting one R, $R_1$ or $R_2$ to another R, $R_1$ or $R_2$ to obtain a compound of formula (I), (c) forming a salt and/or solvate of the obtained compound of formula (I).

Suitable active derivatives of

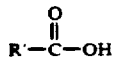

are acid chlorides or acid anhydrides. Another suitable derivative is a mixed anhydride formed between the acid and an alkyl chloroformate.

For example, in standard methods well known to those skilled in the art, the compound of formula (III) may be coupled:

(a) with an acid chloride in the presence of an inorganic or organic base, (b) with the acid in the presence of dicyclohexyl carbodiimide, N-dimethylaminopropyl-N'-ethyl carbodiimide or carbonyl diimidazole, (c) with a mixed anhydride generated in situ from the acid and an alkyl (for example ethyl)chloroformate.

It will be appreciated that a compound of formula (Ia) may be converted to a compound of formula (I), or one compound of formula (I) may be converted to another compound of formula (I), by interconversion of suitable substituents. Thus certain compounds of formula (I) and (Ia) are useful intermediates in forming other compounds of the present invention.

$R_1'$ and $R_2'$ may be alkyl groups and converted to $R_1'/R_2'$ hydrogen atoms by conventional amine dealkylation. When $R_1'$ or $R_2'$ is benzyl or substituted benzyl it may be converted to an $R_1$ or $R_2'$ hydrogen atom by catalytic hydrogenation or other method of reduction. $R_1'$ and $R_2'$ as hydrogen atoms may be converted to $R_1$ and $R_2$ alkyl groups by conventional amine alkylation, or by acylation followed by reduction. $R_1'$ and $R_2'$ are preferably $R_1$ and $R_2$ respectively.

The compound

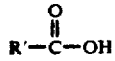

is typically of the formula (IIa)

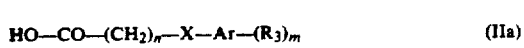

(IIa)

in which $R_3'$ is $R_3$ as defined by formula (II) or a group or atom convertible to $R_3$, the other variables being as defined for formula (II).

Conversions of substituents $R_3'$ on the aromatic group Ar to obtain $R_3$ are generally known in the art of aromatic chemistry. $R_3'$ preferably $R_3$.

The compounds of formula I may be converted into their pharmaceutically acceptable acid addition salts by reaction with the appropriate organic or mineral acids.

Solvates of the compounds of formula I may be formed by crystallization or recrystallization from the appropriate solvent. For example hydrates may be formed by crystallization or recrystallization from aqueous solutions, or solutions in organic solvents containing water.

Also salts or solvates of the compounds of formula I which are not pharmaceutically acceptable may be useful as intermediates in the production of pharmaceutically acceptable salts or solvates. Accordingly such salts or solvates also form part of this invention.

The compounds of formula I exist in more than one stereoisomeric form and the processes of the invention produces mixtures thereof. The individual isomers may be separated one from another by resolution using an optically active acid such as tartaric acid. Alternatively, an asymmetric synthesis would offer a route to the individual form.

The compound of formula (III) may be prepared from a compound of formula (IV) by the reaction scheme shown:

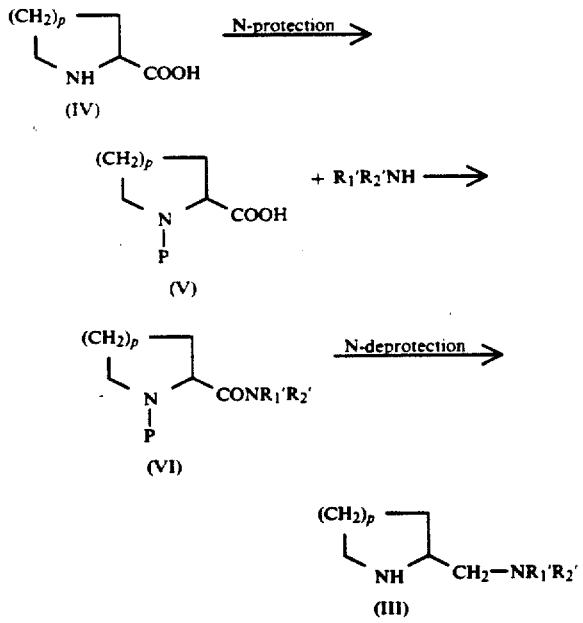

In this scheme, firstly the compound of formula (IV) is nitrogen protected with a conventional protecting group P, such as benzyloxycarbonyl or tert-butyloxycarbonyl, forming the compound of formula (V) which is reacted with the amine $R_1'R_2'NH$ (in which $R_1'$ and $R_2'$ are as defined earlier) to obtain N-protected amide (VI). This is conventionally N-deprotected, for example by catalytic debenzylation if P is benzyloxycarbonyl or by acid treatment if P istert-butyloxycarbonyl, and the resulting basic amide (VII) is reduced to the diamine (III) by reaction with lithium aluminium hydride.

Alternatively, the N-protected acid (V) is reduced to a primary alcohol which is esterified, for example with methane sulfonic acid or p-toluenesulfonic acid, and the ester reacted with $R_1'R_2'NH$. Deprotection of the ring nitrogen gives the diamine (III).

When the starting material of formula (IV) is a racemic mixture, the resulting compounds of formulae (III) and (I) are also racemic. Using a compound of formula (IV) in the R- or S-configuration results in the corresponding optically active products.

The compounds of formula IV are known compounds. When p=1, the compound is R-, S- or R,S-proline. When p=2 it is R-, S-, or R,S-pipecolinic acid (Beilstein 22/IV, 96–97), and when p=3 is it R-, S-, or R,S-hexahydroazepine - 2- carboxylic acid (J. Med. Chem. 14, 501/1971).

Certain of the intermediates described above are novel compounds and, together with the described processes for their preparation, they form a further aspect of this invention.

The activity of the compounds of formula (I) in standard analgesic tests indicates that they are of therapeutic utility in the treatment of pain.

Accordingly the present invention also provides a compound of formula (I), or a pharmaceutically acceptable salt or solvate thereof, for use as an active therepeutic substance.

The present invention further provides a pharmaceutical composition comprising a compound of formula (I), or a pharmaceutically acceptable salt or solvate thereof, and a pharmaceutically acceptable carrier.

The present invention also provides the use of a compound of formula (I), or a pharmaceutically acceptable salt or solvate thereof, in the manufacture of a medicament for the treatment of pain.

Such a medicament, and a composition of this invention, may be prepared by admixture of a compound of the invention with an appropriate carrier. It may contain a diluent, binder, filler, disintegrant, flavouring agent, colouring agent, lubricant or preservative in conventional manner.

These conventional excipients may be employed for example as in the preparation of compositions of known analgesic agents.

Preferably, a pharmaceutical composition of the invention is in unit dosage form and in a form adapted for use in the medical or veterinarial fields. For example, such preparations may be in a pack form accompanied by written or printed instructions for use as an agent in the treatment of pain.

The suitable dosage range for the compounds of the invention depemds on the compound to be employed and on the condition of the patient. It will also depend, inter alia, upon the relation of potency to absorbability and the frequency and route of administration.

The compound or composition of the invention may be formulated for administration by any route, and is preferably in unit dosage form or in a form that a human patient may administer to himself in a single dosage. Advantageously, the composition is suitable for oral, rectal, topical, parenteral, intravenous or intramuscular administration. Preparations may be designed to give slow release of the active ingredient.

Compositions may, for example, be in the form of tablets, capsules, sachets, vials, powders, granules, lozenges, reconstitutable powders, or liquid preparations, for example solutions or suspensions, or suppositories.

The compositions, for example those suitable for oral administration, may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically acceptable setting agents such as sodium lauryl sulphate.

Solid compositions may be obtained by conventional methods of blending, filling, tabletting or the like. Repeated blending operations may be used to distribute the active agent throughout those compositions employing large quantities of fillers. When the composition is in the form of a tablet, powder, or lozenge, any carrier suitable for formulating solid pharmaceutical compositions may be used, examples being magnesium stearate, starch, glucose, lactose, sucrose, rice flour and chalk. Tablets may be coated according to methods well known in normal pharmaceutical practice, in particular with an enteric coating. The composition may also be in the form of an ingestible capsule, for example of gelatin containing the compound, if desired with a carrier or other excipients.

Compositions for oral administration as liquids may be in the form of, for example, emulsions, syrups, or elixirs, or may be presented as a dry product for reconstitution with water or other suitable vehicle before use. Such liquid compositions may contain conventional additives such as suspending agents, for example sorbitol, syrup, methyl cellulose, gelatin, hydroxyethylcellulose, carboxymethylcellulose, aluminium stearate gel, hydrogenated edible fats; emulsifying agents, for example lecithin, sorbitan monooleate, or acacia, aqueous or non-aqueous vehicles, which include edible oils, for example almond oil, fractionated coconut oil, oily esters, for example esters of glycerine, or propylene glycol, or ethyl alcohol glycerine, water or normal saline; preservatives, for example methyl or propyl p-hydroxybenzoate or sorbic acid; and if desired conventional flavouring or colouring agents.

The compounds of this invention may also be administered by a non-oral route. In accordance with routine pharmaceutical procedure, the compositions may be formulated, for example for rectal administration as a suppository. They may also be formulated for presentation in an injectable form in an aqueous or non-aqueous solution, suspension or emulsion in a pharmaceutically acceptable liquid, e.g. sterile pyrogen-free water of a parenterally acceptable oil or a mixture of liquids. The liquid may contain bacteriostatic agents, anti-oxidants or other preservatives, buffers or solutes to render the solution isotonic with the blood, thickening agents, suspending agents or other pharmaceutically acceptable additives. Such forms will be presented in unit dose form such as ampoules or disposable injection devices or in multi-dose forms such as a bottle from which the appropriate dose may be withdrawn or a solid form or concentrate which can be used to prepare an injectable formulation.

As mentioned earlier, the effective dose of compound depends on the particular compound employed, the condition of the patient and on the frequency and route of administration. A unit dose will generally contain from 20 to 1000 mg and preferably will contain from 30 to 500 mg, in particular 50, 100, 150, 200, 250, 300, 350, 400. 450, or 500 mg. The composition may be administered once or more times a day for example 2, 3 or 4 times daily, and the total daily dose for a 70 kg adult will normally be in the range 100 to 3000 mg. Alternatively the unit dose will contain from 2 to 20 mg of active ingredient and be administered in multiples, if desired, to give the preceding daily dose.

Within the above indicated dosage range, no adverse toxicological effects have been observed with compounds of the invention.

The present invention also provides a method of treating pain in mammals, particularly in humans, which comprises administering an effective amount of a compound of formula (I), or pharmaceutically acceptable salt or solvate thereof, to a sufferer.

Compounds of this invention and their preparation are illustrated in the following Examples.

EXAMPLE 1

1-(3,4-dichlorophenyl)acetyl-2-(1-pyrrolidinyl)methyl piperidine hydrochloride 3 g of crude 2-(1-pyrrolidinyl)methyl Piperidine (0,01783 moles) and 4 g of 3,4-dichlorophenylacetic acid (0.0195 moles) were dissolved in 50 ml of dichloromethane. 5 g of dicyclohexylcarbodiimide (0.0267 moles), dissolved in 30 ml of dichloromethane, was added dropwise to the ice-cooled solution. The reaction mixture was left three days at room temperature, then the precipitated dicyclohexylurea was removed by suction filtration, and the solution evaporated to dryness in vacuo. The remaining oil was extracted three times with 2 N-Hydrochloric acid, the combined acid solutions extracted with ether, and the ether solutions discarded. The acid solution was made alkaline with diluted sodium hydroxide, the oily precipitate was extracted with chloroform, and the organic solution evaporated to dryness in vacuo. The oil residue was dissolved in ethyl ether and the solution brought to acidic pH with HCl saturated ether. The solid precipitate was collected by suction filtration and crystallized from 50 ml of methanol.

Yield 3.7 g
M.P. 246° C.
$C_{18}H_{24}Cl_2N_2O.HCl$
M.W. 391.77

| | | | |
|---|---|---|---|
| NMR (DMSO) δ = | 1.35–1.75 | m | 6 H |
| | 1.75–2.10 | m | 4 H |
| | 2.7–4.0 | m | 10 H |
| | 5.0 | m | 1 H |
| | 7.15–7.55 | m | 3 H |
| | 10.3 | broad s | 1 H |

EXAMPLE 2 to 17

The compounds of these Examples were prepared by the same procedure as Example 1, be reacting together the appropriate amine and acid in the presence of dicyclohexylcarbodiimide in dichloromethane, in the same molar ratio of reactants.

The compounds and starting materials are summarised as follows, with NMR characterising data. Other characteristics of Examples 1 to 17 are summarised Table 1A and 1B.

The compounds in Table 1B are racemates, except in the case of Example 16 which is a diastereoisomer of unassigned configuration separated from the originally obtained diastereoisomeric mixture.

EXAMPLE 2

1-(3,4-dichlorophenyl)acetyl-2-dimethylaminomethyl piperidine hydrochloride

Prepared from 2-dimethylaminomethyl piperidine and 3,4-dichlorophenylacetic acid.

| | | | |
|---|---|---|---|
| NMR (DMSO) δ = | 1.35–1.70 | m | 6 H |
| | 2.75 | s | 6 H |
| | 2.9–4.0 | m | 6 H |
| | 5.0 | m | 1 H |
| | 7.15–7.65 | m | 3 H |
| | 10.3 | broad s | 1 H |

EXAMPLE 3

(2R)-1-(3,4-dichlorophenylacetyl)-2-(1-pyrrolidinylmethyl)piperidine hydrochloride hydrate.

Prepared from (2R)-2-(1 pyrrolidinyl methyl) piperidine and 3,4-dichlorophenylacetic acid.

| | | | |
|---|---|---|---|
| NMR (DMSO) δ = | 1.35–1.75 | m | 6 H |
| | 1.75–2.10 | m | 4 H |
| | 2.7–4.0 | m | 10 H |
| | 5.0 | m | 1 H |
| | 7.15–7.65 | m | 3 H |
| | 10.45 | 1.broad s | 1 H |

EXAMPLE 4

-(2S)-1-(3,4-dichlorophenylacetyl)-2-(1-pyrrolidinylmethyl)piperidine hydrochloride hydrate.

Prepared from (2S)-2-(1-pyrrolidinyl methyl) piperidine and 3,4-dichlorophenylacetic acid.

| | | | |
|---|---|---|---|
| NMR (DMSO) δ = | 1.35–1.75 | m | 6 H |
| | 1.75–2.10 | m | 4 H |
| | 2.7–4.0 | m | 10 H |
| | 5.0 | m | 1 H |
| | 7.15–7.65 | m | 3 H |
| | 10.4 | 1.broad s | 1 H |

EXAMPLE 5

-(2S)-1-(3,4-dichlorophenylacetyl)-2-dimethylamino methylpiperidine sesquihydrate:

Prepared from (2S)-2-dimethylaminomethyl piperidine and 3,4-dichlorophenylacetic acid.

| | | | |
|---|---|---|---|
| NMR (DMSO) δ = | 1.35–1.70 | m | 6 H |
| | 2.75 | s | 6 H |
| | 2.9–4.0 | m | 6 H |
| | 5.0 | m | 1 H |
| | 7.15–7.65 | m | 3 H |
| | 10.3 | broad s | 1 H |

EXAMPLE 6

-1-(3,4-dichlorophenylacetyl)-2-(1-pyrrolidinylmethyl) pyrrolidine hydrochloride.

Prepared from 2-(1-pyrrolidinylmethyl)pyrrolidine and 3,4-dichlorophenylacetic acid.

EXAMPLE 7

-1-(3,4-dichlorophenylacetyl)-2-dimethylaminomethyl pyrrolidine hydrochloride.

Prepared from 2-dimethylaminomethyl pyrrolidine and 3,4-dichlorophenylacetic acid.

EXAMPLE 8

-1-(3,4-dichlorophenylacetyl)-2-(1-pyrrolidinylmethyl)-hexahydroazepine hydrochloride.

Prepared from 2-(1-pyrrolidinylmethyl)hexahydroazepine and 3,4-dichlorophenylacetic acid.

EXAMPLE 9

-1-(3,4-dichlorophenylacetyl)-2-dimethylaminomethyl-hexahydroazepine hydrochloride hydrate.

Prepared from 2-dimethylaminomethylhexahydroazepine and 3,4-dichlorophenylacetic acid.

EXAMPLE 10

-1-phenylacetyl-2-(1-pyrrolidinylmethyl)piperidine hydrochloride.

Prepared from 2-(1-pyrrolidinylmethyl)piperidine and phenylacetic acid.

| | | | |
|---|---|---|---|
| NMR ($CDCl_3$) δ = | 1.3–1.9 | broad s | 6 H |
| | 1.9–2.3 | broad s | 4 H |
| | 2.6–3.1 | broad s | 3 H |
| | 3.3–4.2 | m | 4 H |
| | 3.9 | s | 2 H |
| | 5.2 | m | 1 H |
| | 7.3 | s | 5 H |

EXAMPLE 11

-1-(3,4-dimethylphenylacetyl)-2-(1-pyrrolidinylmethyl) piperidine hydrochloride.

Prepared from 2-(1-pyrrolidinylmethyl)piperidine and 3,4-dimethylphenylacetic acid.

EXAMPLE 12

1-(5-indaneacetyl)-2-(1-pyrrolidinylmethyl)piperidine hydrochloride.

Prepared from 2-(1-pyrrolidinylmethyl)piperidine and 5-indaneacetic acid.

| | | | |
|---|---|---|---|
| NMR ($CDCl_3$) δ = | 1.1–2.5 | m | 12 H |
| | 2.5–3.1 | m | 7 H |
| | 3.1–4.2 | m | 7 H |
| | 5.2 | m | 1 H |
| | 7.15 | m | 3 H |

EXAMPLE 13

1-(6-tetralylacetyl)-2-(1-pyrrolidinylmethyl)piperidine hydrochloride.

Prepared from 2-(1-pyrrolidinylmethyl)piperidine and 6-tetralylacetic acid.

EXAMPLE 14

1-(4-chlorophenylacetyl)-2-(1-pyrrolidinylmethyl) piperidine hydrochloride.

Prepared from 2-(1-pyrrolidinylmethyl)piperidine and 4-chlorophenylacetic acid.

| | | | |
|---|---|---|---|
| NMR ($CDCl_3$) δ = | 1.4–1.8 | broad s | 6 H |
| | 1.9–2.4 | m | 4 H |
| | 2.5–3 | m | 3 H |
| | 3.2–4.2 | m | 5 H |
| | 3.9 | q | 2 H |
| | 5.3 | m | 1 H |
| | 7.2 | s | 4 H |

EXAMPLE 15

1-(3-4-dimethoxyphenylacetyl)-2-(1-pyrrolidinyl-methyl) piperidine hydrochloride.

Prepared from 2-(1-pyrrolidinylmethyl)piperidine and 3,4-dimethoxyphenylacetic acid.

EXAMPLE 16

1-(2-phenylbutyroil)-2-(1pyrrolidinylmethyl) piperidine hydrochloride. Isomer B

Prepared from 2-(1-pyrrolidinylmethyl)piperidine and 2-phenylbutyric acid. After working-up the reaction mixture as described in Example 1, a mixture of two diastereoisomeric hydrochlorides was obtained. It was dissolved in a minimum amount of water, the solution made alkaline with 5% sodium hydroxide solution, the precipitated oil extracted with methylene chloride, the organic solution dried on sodium sulphate and evaporated to dryness in vacuo. The resulting oily mixture (diastereoisomeric bases) was chromatographed on a silica gel column, eluting first with methylene chloride, amd subsequently with methylene chloride containing increasing amounts of methanol (0.5% to 2.2%). The slow-descending compound, identified as diastereoisomer B (while the fast-moving one was identified as diastereoisomer A) was collected, dissolved in ether, and the solution made acidic with HCL-saturated ether. The precipitated solid was crystallized from acetone/ethanol. M.P. 210°-1° C. The diastereoisomer A was transformed into the hydrochloride in the same way. M.P. 177°-80° C.

EXAMPLE 17

1-(4-chlorophenoxyacetyl)-2-(1-pyrrolidinylmethyl) piperidine hydrochloride.

Prepared from 2-(1-pyrrolidinylmethyl)piperidine and 4-chlorophenoxyacetic acid.

| | | | |
|---|---|---|---|
| NMR ($CDCl_3$) δ = | 1.3–1.9 | broad s | 6 H |
| | 1.9–2.5 | m | 4 H |
| | 2.5–3.1 | m | 3 H |
| | 3.2–4.2 | m | 5 H |
| | 4.95 | s | 2 H |
| | 5.0–5.35 | m | 1 H |
| | 5.9–7.3 | m | 4 H |

TABLE IA

SUMMARY OF EXAMPLES

General Formula 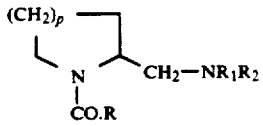

| EXAMPLE NO. | p | R | $R_1$ | $R_2$ | Stereochemistry at Carbon 2 | Molecular formula | Molecular Weight | Melting Point | $[\alpha]_D$ |
|---|---|---|---|---|---|---|---|---|---|
| 1 | 2 | 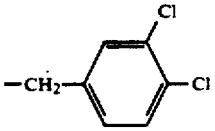 | $R_1R_2$ = 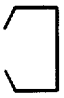 | | R,S | $C_{18}H_{24}Cl_2N_2O.HCl$ | 391.77 | 246 | — |
| 2 | 2 | " | $-CH_3$ | $-CH_3$ | R,S | $C_{16}H_{22}Cl_2N_2O.HCl$ | 365.731 | 207 | — |
| 3 | 2 | " | $R_1R_2$ = 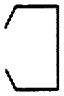 | | R | $C_{18}H_{24}Cl_2N_2O.HCl.H_2O$ | 409.783 | 159–60 | +47.6 (c = 2 MeOH) |
| 4 | 2 | " | | " | S | $C_{18}H_{24}Cl_2N_2O.HCl.H_2O$ | 409.783 | 160–1 | −49. (c = 2 MeOH) |
| 5 | 2 | " | $-CH_3$ | $-CH_3$ | S | $C_{16}H_{22}Cl_2N_2O.HCl.1.5H_2O$ | 392.755 | 196–7 | −34.5 (c = 0.33 MeOH) |
| 6 | 1 | " | $R_1R_2$ = 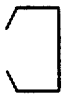 | | R,S | $C_{17}H_{22}Cl_2N_2O.HCl$ | 377.741 | 191 | — |
| 7 | 1 | " | $-CH_3$ | $-CH_3$ | R,S | $C_{15}H_{20}Cl_2N_2O.HCl$ | 351.705 | 175 | — |
| 8 | 3 | " | $R_1R_2$ = 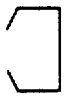 | | R,S | $C_{19}H_{26}Cl_2N_2O.HCl$ | 405.793 | 238 | — |
| 9 | 3 | " | $-CH_3$ | $-CH_3$ | R,S | $C_{17}H_{24}Cl_2N_2O.HCl.H_2O$ | 397.773 | 212 | — |

TABLE IB

SUMMARY OF EXAMPLES

General Formula 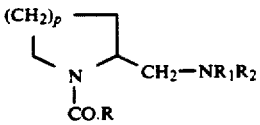 in which p is 2, $R_1$ and $R^2$ are 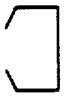

| Example No. | R | Salt | Molecular Formula | Molecular Weight | Melting Point (°C.) |
|---|---|---|---|---|---|
| 10 | 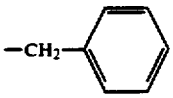 | HCl | $C_{18}H_{27}N_2OCl$ | 322.869 | 217–9 |

TABLE IB-continued

SUMMARY OF EXAMPLES

General Formula 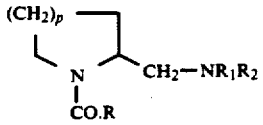 in which p is 2, $R_1$ and $R^2$ are 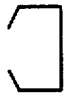

| Example No. | R | Salt | Molecular Formula | Molecular Weight | Melting Point (°C.) |
|---|---|---|---|---|---|
| 11 | 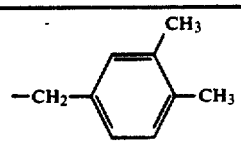 | HCl | $C_{20}H_{31}N_2OCl$ | 350.921 | 165–6 |
| 12 | 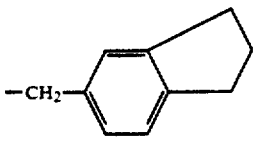 | HCl | $C_{21}H_{31}N_2OCl$ | 362.931 | 181–4 |
| 13 | 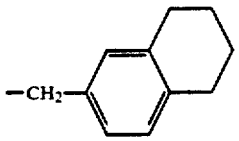 | HCl | $C_{22}H_{33}N_2OCl$ | 376.957 | 182–5 |
| 14 | 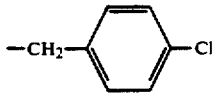 | HCl | $C_{18}H_{26}N_2OCl$ | 357.318 | 200–2 |
| 15 | 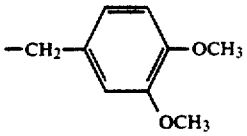 | HCl | $C_{20}H_{31}N_2O_3Cl$ | 382.92 | 168–70 |
| 16 | 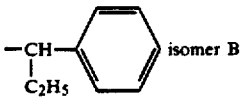 isomer B | HCl | $C_{20}N_{31}N_2OCl$ | 350.921 | 210–1 |
| 17 | 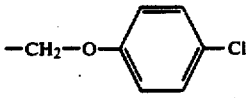 | HCl | $C_{18}H_{26}N_2O_2Cl_2$ | 373.318 | 185–7 |

The pharmacological activity of the compounds of this invention is illustrated by various in vitro and in vivo models, using the following test procedures, in which the mouse p-phenylquinone writhing test and mouse tail flick test demonstrate analgesic activity.

The results of the tests are given in Tables 2 and 3.

Mouse Tail-flick test (Modified from the procedure published by D'Amour et al., J. Pharm. Exptl. Ther. 72, 74/1941)

Male Charles River mice, average weight 26 g, are used. Selection is carried out before beginning of experiments: only mice whose reaction time is less than 8 sec are used. They are randomly distributed into groups of 10 and dosed with compounds under test, with positive and negative controls being included.

Compounds under test are administered subcutaneously in isotonic saline in a volume of 20 ml. $Kg^{-1}$. 30 min later mice are placed again under heat source (Socrel apparatus) and reaction time is recorded.

The analgestic activity of the test compound is expressed as the percent number of mice doubling the initial time within a group.

$$\% \text{ analgesia} = \frac{\text{No. of mice doubling the reaction time}}{\text{Total no. of mice per group}} \times 100$$

Mouse p-phenylquinone Writhing test (According to Siegmund et al., Proc. Soc. Exptl. Biol. 95, 729/1957)

Male Charles River mice, average weight 26 g, are randomly distributed into group of 10 and are dosed subcutaneously with compounds under test, dissolved in isotonic saline (20 ml.$Kg^{-1}$). The experiments are carried out in the presence of positive and negative controls. 20 min after the mince are injected intraperitoneally with p-phenylquinone 0.02%, 10 ml. $Kg^{-1}$, maintained at 37° C. in a water bath. The mice are placed in a perspex compartmented observation box and observed for a period of 8 min after injection of p-phenylquinone. The dose-response curve is obtained by basing observation on the all or none response.

Analgestic activity is calculated as percentage of animals completely protected from writhing in an 8 min period:

$$\% \text{ analgesia} = \frac{\text{No. of mice failing to writhe}}{\text{Total no. of mice per group}} \times 100$$

RECEPTOR AFFINITY STUDY Tissue preparation

Radio receptor binding to $\mu$ and K sites is performed on fresh guinea pig brain homogenate prepared according to Kosterlitz (1981).

Whole brain without cerebellum is homogenized in 50 mM, Tris-buffer (pH 7.4 at 0° C.) and centrifuged at 49.000×g×10 min.

The pellet is then resuspended in the same buffer, incubated at 37° C. for 45 min. and centrifuged again.

1.9 ml of the final homogenate (1:100 in Tris-pH 7.4, 0° C.) is used for the binding assay.

Binding to $\mu$ sites (Magnan J., 1982)

$^3$H [D-Ala$^2$, MePhe$^4$, Gly-ol$^5$] Enkephalin ($^3$H-DAGO), an enkephalin analogue that binds selectively to $\mu$ receptor, is added to the biological substrate and incubated at 25° C. for 40 min., filtered through Whatman GF-C and washed with ice-cold Tris-buffer.

The filters are then dryed, solubilized in Filtercount and the radioactivity monitored. Non specific binding is determined in the presence of $10^{-6}$M Naloxone.

Binding to K sites (Magnan J., 1982)

The binding of tritiated Ethylketocyclazocine to brain homogenate is measured the in presence of 100 nanomolar D-Ala-D-LeuEnkephalin (DADLE) and 100 nanomolar DAGO, added to saturate the $\delta$ and $\mu$ opioid receptors respectively.

Final homogenate with solutions of the cold ligand and of the labelled ligand is incubated for 40 min. at 25° C., filtered through Whatman GF/C glass filter discs and washed.

The radioactivity bound to the filters is counted by liquid scintillation spectrophotometry.

MR 2266.500 nM is utilized to determine the saturable binding.

For the calculation of the kinetic parameters of the binding of labelled and unlabelled ligands, the equilibrium dissociation constant ($K_D$), the inhibition constant (Ki) and the maximum number of binding sites (B max) are determined from saturation curves and competition experiments (Hill 1910; Scatchard 1949; Cheng and Prusoff 1973; Gillan et al. 1980).

A concentration of radioligand near $K_D$ is used in the binding assays evaluating our compounds.

| | |
|---|---|
| Hill, A. V. (1910) | J. Physiol. 40, IV-VIII (1910) |
| Scatchard G. (1949) | Ann. N.Y. Acad. Sci., 51, 660-674 |
| Cheng and Prusoff W. H. (1973) | Biochem. Pharmac. 22, 3099-3102 |
| Gillan M. G. C., Kosterlitz H. W. and Paterson S. Y. (1980) | Br.J. Pharmac. 70, 481-490 |
| Kotsterliz H. W., Paterson S. Y. and Robson L. E. (1981) | Br.J. Pharmac. 73, 939-949 |
| Magnan J., Paterson S. Y., Tavani A., and Kosterlits H. W. (1982) | Arch. Pharmacol. 319, 197-205 |

TABLE 2

| Example Nos. | PHARMACOLOGICAL DATA IN VIVO TESTS - $ED_{50}$ mg $Kg^{-1}$ s.c. Mouse tail flick | Mouse p-phenylquinone writhing | RECEPTOR BINDING - $K_i$ (nM) $\mu$ | K |
|---|---|---|---|---|
| 1 | 0.11 | 0.20 | 1860 | 1.83 |
| 2 | 0.36 | 0.65 | 3730 | 8.21 |
| 3 | 17.5 | 12.4 | 7110 | 62.1 |
| 4 | 0.055 | 0.12 | 1559 | 0.77 |
| 5 | 1.03 | 0.44 | >1.000 | 5.01 |
| 8 | 8.76 | — | N.E. | 6.51 |

TABLE 3

| Example Nos. | MOUSE TAIL FLICK SUBCUTANEOUS % Protection 1 mg $Kg^{-1}$ | $ED_{50}$ mg/$Kg^{-1}$ | ORAL $ED_{50}$ mg/Kg os | OPIATE RECEPTOR BINDING Ki(nm) or % residual specific binding at $10^{-6}$ M $\mu$ | K |
|---|---|---|---|---|---|
| 10 | 40 | — | — | — | 100% |
| 11 | 60 | — | — | — | 67% |
| 12 | 60 | — | — | — | 62% |
| 13 | 80 | 45 | 3.91 | 500 | 5.72 |
| 14 | 40 | — | — | — | 61% |
| 15 | 40 | — | — | — | 100% |
| 16 | 40 | — | — | — | — |
| 17 | 80 | 91 | — | — | 9.54 |

We claim:

1. A compound of formula I:

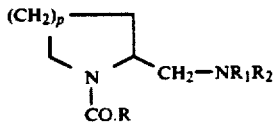

(I)

or a solvate or pharmaceutically acceptable salt thereof in which R has the formula (II):

$$-(CHR_4)_n-X-Ar-(R_3)_m \quad \text{(II)}$$

in which n is 0, 1 or 2, m is 0, 1 or 2,

X is a direct bond, or O, S or $NR_5$, in which $R_5$ is hydrogen or $C_{1-6}$ alkyl, Ar is phenyl or thienyl, $R_3$ is halogen, $C_{1-6}$ alkoxy, cyano, $-COOR_4$, $C_{1-6}$ alkyl, or amino or, when m is 2, two $R_3$'s form a $C_{3-6}$ polymethylene group, and $R_4$ is hydrogen or $C_{1-6}$ alkyl, $R_1$ and $R_2$ are [independently $C_{1-6}$ alkyl or together form a $C_{3-6}$ polymethylene or $C_{3-6}$ alkenylene group] *each methyl or together with the nitrogen atom to which they are attached form 1-pyrrolidinyl;* and p is 1, 2, 3 or 4.

2. A compound according to claim 1, in which each of $R_1$ and $R_2$ is methyl[, ethyl, propyl, butyl, pentyl or hexyl].

3. A compound according to claim 1, in which $R_1$ and $R_2$ together *with the nitrogen atom to which they are attached* form [a propylene, butylene, pentylene or hexylene group] *1-pyrrolidinyl.*

[4. The compound according to claim 1, in which $R_1$ and $R_2$ together form a $-CH_2-CH=CH-CH_2-$ group.]

5. A compound according to claim 1, in which Ar is phenyl.

6. A compound according to claim 1 in which p is 2.

7. A compound selected from:

1-(3,4-dichlorophenyl)acetyl-2-(1-pyrrolidinyl)-methyl piperidine hydrochloride, 1-(3,4-dichlorophenyl)acetyl-2-dimethylaminomethyl piperidine hydrochloride, (2R)-1-(3,4-dichlorophenylacetyl)-2-(1-pyrrolidinyl-methyl)piperidine hydrochloride hydrate, -(2S)-1-(3,4-dichlorophenylacetyl-2-(1-pyrrolidinyl-methyl)piperidine hydrochloride hydrate, -(2S)-1-(3,4-dichlorophenylacetyl)-2-dimethylaminomethylpiperidine sesquihydrate, -1-(3,4-dichlorophenylacetyl-2-(1-pyrrolidinylmethyl)pyrrolidine hydrochloride, -1-(3,4-dichlorophenylacetyl-2-dimethylaminomethyl-pyrrolidine hydrochloride, -1-(3,4-dichlorophenylacetyl-2-(1-pyrrolidinylmethyl)hexahydroazepine hydrochloride, -1-(3,4-dichlorophenylacetyl-2-dimethylaminomethylhexahydroazepine hydrochloride hydrate, -1-phenylacetyl-2-(1-pyrrolidinylmethyl)piperidine hydrochloride, 1-(3,4-dimethylphenylacetyl)-2-(1-pyrrolidinylmethyl)piperidine hydrochloride, 1-(5-indaneacetyl)-2-(1-pyrrolidinylmethyl)piperidine hydrochloride, 1-(6-tetralylacetyl)-2-(1-pyrrolidinylmethyl) piperidine hydrochloride, 1-(4-chlorophenylacetyl)-2-(1-pyrrolidinylmethyl) piperidine hydrochloride, 1-(3,4-dimethoxyphenylacetyl-2-(1-pyrrolidinylmethyl)piperidine hydrochloride, 1-(2-phenylbutyroil)-2-(1-pyrrolidinylmethyl) piperidine hydrochloride, 1-(4-chlorophenoxyacetyl)-2-(1-pyrrolidinylmethyl) piperidine hydrochloride.

8. A pharmaceutical composition for treating pain in mammals, comprising an effective amount of a compound according to claim 1, and a pharmaceutically acceptable carrier.

9. A composition according to claim 8 in unit dosage form.

10. A method of treating pain in mammals which comprises administering an effective non-toxic amount of a compound according to claim 1 to a sufferer.

* * * * *